United States Patent [19]
Lowell et al.

[11] Patent Number: 5,471,293
[45] Date of Patent: Nov. 28, 1995

[54] METHOD AND DEVICE FOR DETERMINING DEFECTS WITHIN A CRYSTALLOGRAPHIC SUBSTRATE

[75] Inventors: John K. Lowell, Round Rock; Mohammed Anjum, Austin; Valerie A. Wenner, Austin; Norman L. Armour, Austin; Maung H. Kyaw, Austin, all of Tex.

[73] Assignee: Advanced Micro Devices, Sunnyvale, Calif.

[21] Appl. No.: 191,387

[22] Filed: Feb. 2, 1994

[51] Int. Cl.$^6$ ............................................. G01N 21/00
[52] U.S. Cl. ............................................. 356/30; 356/432
[58] Field of Search ............................. 356/30, 432, 342

[56] References Cited

U.S. PATENT DOCUMENTS 4,567,431 1/1986 Goodman .......................... 324/158 D
5,025,145 6/1991 Lagowski .

OTHER PUBLICATIONS

Lagowski, et al., "Non–Contact Mapping of Heavy Metal Contamination for Silicon IC Fabrication", (1992), pp. A185–A192.

Moore, "Theory and Experiment on the Surface–Photovoltage Diffusion–Length Measurement as Applied to Amorphous Silicon", *American Institute of Physics*, (1983), pp. 222–228.

*Primary Examiner*—Richard A. Rosenberger
*Attorney, Agent, or Firm*—Kevin L. Daffer

[57] ABSTRACT

A method and device is provided for determining defects within a single crystal substrate. The methodology includes a surface photovoltage (SPV) technique in which the magnitude of non-linearity is quantified and correlated to defects within the crystal lattice. The correlation factor is determined in a rapid and efficient manner using least square correlation methodology without having to determine diffusion length and incur difficulties associated therewith. Obtaining a quantifiable least square correlation factor allows the operator to quickly determine the amount of crystalline damage often encountered by, for example, ion implantation. In addition, the operator can determine the relative depth and position of defective crystalline layers within the substrate based upon demarcations between monotonically and non-monotonically aligned points plotted in a graph of reciprocal photovoltage versus reciprocal absorption coefficient.

16 Claims, 3 Drawing Sheets

5,471,293

METHOD AND DEVICE FOR DETERMINING DEFECTS WITHIN A CRYSTALLOGRAPHIC SUBSTRATE

BACKGROUND OF THE INVENTION

1. Field of the Invention

This invention relates to a method and device for determining defects within a crystallographic substrate and more particularly to non-contact, non-destructive detection of defects within the substrate.

2. Description of the Relevant Art

Surface photovoltage (SPV) techniques for measuring the presence of heavy metal contaminants are well known. SPV detection of metal contaminants generally includes many steps. SPV utilizes light directed upon a semiconductor and, if the energy of the incident light (photons) is above the semiconductor bandgap, $E_g$, then the incident photons are absorbed and produce excess carriers (holes and electrons). The concept of directing photons upon a substrate and producing minority carriers is often described as the recombination or "photogeneration" process. As minority carriers are photogenerated by the impinging photons, a certain number of the carriers reach the proximity of the substrate surface and become separated by the electric field of the surface space charge region to produce photovoltage.

The amount of minority carriers which reach the surface and are detected as photovoltage is directly proportional to the amount of recombination centers within a substrate. Many researchers have discovered a correlation between the presence of heavy metal contaminants and the introduction of recombination centers within the substrate bandgap. See, e.g., Lagowski, et al., "Non-Contact Mapping of Heavy Metal Contamination for Silicon IC Fabrication", (IOP Publishing, Ltd. 1992) pp. A185–A192 (herein incorporated by reference). Heavy metal introduction of recombination centers will increase the likelihood that minority carriers will diffuse to a lesser extent through a semiconductor during their lifetime. Accordingly, presence of heavy metal contaminants set forth a reduction in diffusion length L. Thus, SPV has been successfully used as a technique for quantifying heavy metal contaminants by determining fluctuations in L.

Measurement of diffusion length L begins by measurement of photovoltage and photon flux at several wavelengths of incident photon energies. The magnitude of the photovoltage is varied by adjustment of the incident light intensity or photoflux. Photovoltage at each light intensity value is plotted in relation to the reciprocal absorption coefficient, $\propto^{-1}$. The plot is then linearly extrapolated to determine the intercept point along the reciprocal coefficient axis to obtain the minority carrier diffusion length L. L corresponds to the distance along the reciprocal coefficient axis at points in which the reciprocal absorption coefficient are negative. A general outline of the technique for measuring diffusion length L and correlating diffusion length L to the presence of heavy metal contaminants is described in U.S. Pat. No. 5,025,145 (herein incorporated by reference).

The determination of diffusion length and the correlation of diffusion length to heavy metal contaminants is well founded in the principle of defining reciprocal photovoltage as a linear function to reciprocal absorption coefficient. However, it is well known that reciprocal photovoltage is not always a linear (monotonically increasing) function of reciprocal absorption coefficient. Several points in the plot of reciprocal photovoltage versus reciprocal absorption coefficient may not satisfy the monotonically increasing criteria. In such case, points which do not meet the monotonically increasing criteria are rejected from the computation of the diffusion length. Only those points which are linear are utilized for extrapolation and computation of diffusion length L.

While determination of diffusion length L is well suited for detecting metal impurities, the procedure is often burdensome. First, the procedure requires the rejection of non-linear points from the computation model. It is oftentimes difficult to determine which points must be rejected (i.e., which points fall outside the monotonically increasing criteria). If certain "valid" points are rejected and certain points which should be "invalid" are accepted, then the extrapolated diffusion length L will be inaccurate. Thus, the data processor which accumulates photovoltages and performs the criteria modeling must be well attuned to accept only valid points while rejecting all invalid points. Secondly, the procedure requires a full mapping of each point in order to extrapolate valid points along a straight line to an x-axis intersect point (representative of diffusion length L). The x-intercept methodology and full extrapolation technique can be time consuming.

Although diffusion length L has been well studied and is generally accepted in the industry as an important application of SPV in the non-destructive detection of heavy metal contaminants, other techniques which utilize SPV for measuring other properties of the substrate have not been properly studied and applied to semiconductor manufacture. Specifically, during fabrication upon and into a crystallographic substrate, damage can occur at various points within the substrate. The damage can be present within the initial starting material or can occur during subsequent fabrication steps and present itself as defects within the crystallographic substrate. As defined herein, crystallographic refers to single crystal material such as single crystal silicon. As further defined herein, "defects" refers to any non-uniform material or structure present within a crystallographic (single crystal) uniform substrate. The defect material or structure can be present in the initial substrate starting material or can arise from ion implantation. Exemplary defects include areas of lattice dislocation caused, for example, by (i) an excessive concentration of diffusant, (ii) slippage caused by thermally induced stress, or (iii) ion implantation.

Anneal may not always remove implant-induced defects. Thus, it is important to be able to detect the occurrence of such defects at each of the processing steps. By using a non-contact, non-destructive method, the wafer can be maintained throughout the processing steps and defects can be charted in order to determine their source. Additionally, it would be advantageous to determine the relative success of anneal in removing crystallographic defects caused by ion implantation such that, if necessary, additional anneal steps at possibly higher temperatures can be utilized.

It would be further advantageous to provide a method for determining crystallographic defects using the advantages of SPV techniques but without having to incur the burdensome disadvantages of determining diffusion length L. The problems of determining non-linear points, rejecting non-linear points, and extrapolating diffusion length are to be avoided if the methodology for determining crystallographic defects is to be both efficient and rapid.

SUMMARY OF THE INVENTION

The problems outlined above are in large part solved by the method and device of the present invention. That is, a method is provided for determining defects within a crystallographic substrate without requiring the identification or extrapolation of diffusion length L. Moreover, the method purposefully avoids determining non-linear points and rejecting said points within a reciprocal photovoltage and reciprocal absorption plot. By determining non-linear points (points which are not monotonically increasing) as well as linear points (monotonically increasing points) and without having to discern between the two, the present methodology achieves a more efficient and faster determination of defects within a crystallographic substrate. Diffusion length extrapolation from accepted linear points and the burdensome procedures associated therewith are purposefully avoided by the present methodology.

Broadly speaking, the present invention contemplates a method for determining defects within a crystallographic substrate. The method includes the SPV technique of radiating a crystallographic substrate with a plurality of dissimilar photon energies to produce a respective plurality of photovoltages. A plurality of absorption coefficients corresponding to the respective plurality of photovoltages are obtained, and the reciprocal photovoltages and reciprocal absorption coefficients can be mapped to produce a set of observed points. The observed points are plotted for each photon energy of radiating light placed upon the substrate. An important advantage associated with the present invention is the quick and efficient computation of a least square correlation factor between the set of observed points and a linear, sloped line. The sloped line is purposefully limited to the positive reciprocal absorption values and need not be extrapolated as in prior diffusion length measurement techniques. Once the least square correlation factor is determined, the presence of defects is found to be inversely proportional to that factor. If the least square correlation factor becomes less than a pre-determined amount, then the operator can determine the presence of crystallographic defects.

By using a rapidly compiled least square correlation methodology, the non-contact, non-destructive detection method hereof can be performed quickly and easily by a data processor which receives reciprocal absorption coefficients and corresponding photovoltages and easily produces a least square correlation factor based upon a set of expected, monotonically increasing points. The computing steps generally include obtaining a set of expected points along a linear sloped line for each of the plurality of photovoltages. Once the expected points are modeled and the observed points are obtained, the processor then calculates the differences between the expected points and the observed points at each reciprocal photovoltage value or reciprocal absorption coefficient value. Each difference is then divided by a scaling factor to obtain a scaled difference less than one. The scaled differences for each of the observed points are squared to produce a plurality of scaled squared differences. The scaled squared differences are then added to obtain a squared sum. A square root of the squared sum produces a residual least square correlation factor, wherein the residual least square correlation factor is subtracted from one to produce a least square correlation factor. The magnitude of the least square correlation factor is inversely proportional to the amount of defects within the substrate. If the substrate is "clean" and no defects exists within an ideal crystallographic substrate, then the least square correlation factor is substantially equal to one. However, as defects arise within the crystallographic substrate or lattice, then the correlation factor will decrease below one (e.g., least squared correlation factor can drop below 0.98 thereby indicating possible defects).

The present invention further contemplates a more efficient and faster detection methodology which excludes all observed points having a reciprocal absorption coefficient less than 0 μm. Thus, all observed points having a reciprocal absorption coefficient greater than 0 μm, regardless of whether the observed points are monotonically increasing, are included in the mapping criteria. Thus, an initial classification of monotonically versus non-monotonically increasing points, and the time required for such determination, is purposely avoided. Still further, the present invention contemplates a method for non-contact, non-destructive determination of defects while avoiding the determination of diffusion length, and problems associated therewith.

The present invention still further contemplates a device for determining defects within a semiconductor substrate. The device includes a light source adapted to produce a plurality of light beams at dissimilar wavelengths (at dissimilar photon energies). A housing is connected to the light source and is capable of movement across an upper surface of a semiconductor substrate. The housing is adapted to receive a fiber optic cable containing the plurality of light beams and to house a photodetector adapted for producing a respective plurality of photovoltages responsive to the light beams which are directed upon the substrate. A lock-in amplifier is connected to the housing and the light source for locking in the photovoltages with the phase of respective light beam wavelengths. A data processor is connected to the lock-in amplifier for (i) compiling a set of expected points upon a straight line, (ii) mapping a set of observed points corresponding to the plurality of photovoltages, (iii) computing a least square correlation factor between the set of observed points and respective set of expected points, and (iv) ascertaining the presence of defects within the semiconductor substrate based upon the magnitude of the least square correlation factor being less than a predetermined amount.

BRIEF DESCRIPTION OF THE DRAWINGS

Other objects and advantages of the invention will become apparent upon reading the following detailed description and upon reference to accompanying drawings in which.

Figure 1:
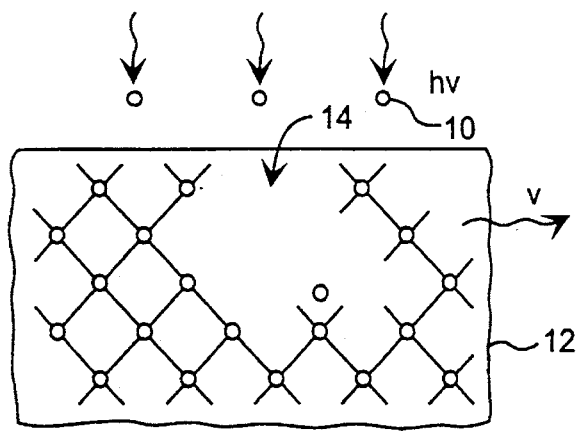
FIG. 1 is an atomic level diagram of an SPV process utilized for detecting the presence of crystallographic defects according to the present invention.

While the invention is susceptible to various modifications and alternative forms, specific embodiments thereof are shown by way of example in the drawings and will herein be described in detail. It should be understood, however, that the drawings and description thereto are not intended to limit the invention to the particular forms disclosed, but on the contrary, the intention is to cover all modifications, equivalents, and alternatives falling within the spirit and scope of the present invention as defined by the appended claims.

DETAILED DESCRIPTION OF THE INVENTION

Turning now to FIG. 1, an atomic diagram is shown illustrative of the lattice network within a crystalline silicon substrate as well as defects or disruptions within the lattice. Minority carriers 10 (either holes or electrons) are injected into silicon substrate 12 at photon energies hv. Various defect sites 14 may occur within the single crystal lattice and, based upon the amount of defect within the lattice, changes in photovoltage V occur as a result of recombination effect in SPV technique. The presence and quantity of defects within the lattice can be determined by a proportional reduction in photovoltage V. An annealing step which occurs after ion implantation does not, in all instances, remove the lattice damage. A preferred result of the present methodology is therefore well suited for determining the relative success of the anneal step by comparing photovoltage outcome before and after anneal. Moreover, photovoltage V can be obtained insitu without destroying or contacting the wafer.

The physical mechanism involved in the production of surface photovoltage involves the injection of minority carriers, wherein the injected minority carriers form a depletion region. The depletion region is a function of the holes and electrons moving in opposite directions along lattice lines. If the lattice is undamaged (i.e., no defects) then there is no abnormalities associated with the formation of the depletion region. However, if the lattice structure is damaged, then the depletion region formation causes abnormalities in the SPV readings. Importantly, defect density is oftentimes a function of the defect location with substrate 12. Oftentimes, there is a lesser number of lattice defects at deeper depths than at shallower depths. As photon energies are increased in order to reach the deeper depths, resulting surface photovoltage will indicate a corresponding lesser amount of defects at the deeper depths. Thus, the present methodology is well suited for determining relative defect locations at varying depths within substrate 12. By merely changing photon energy, various depths can be probed in a non-intrusive manner.

Not only can relative changes in defects be measured as well as the relative location of those defects, but also the defect amounts can be quantified in a less time-consuming manner than conventional techniques. A popular conventional technique requires breaking the wafer and performing a cross-sectional transmission electron microscopy (XTEM) analysis on the resulting pieces.

Figure 2:
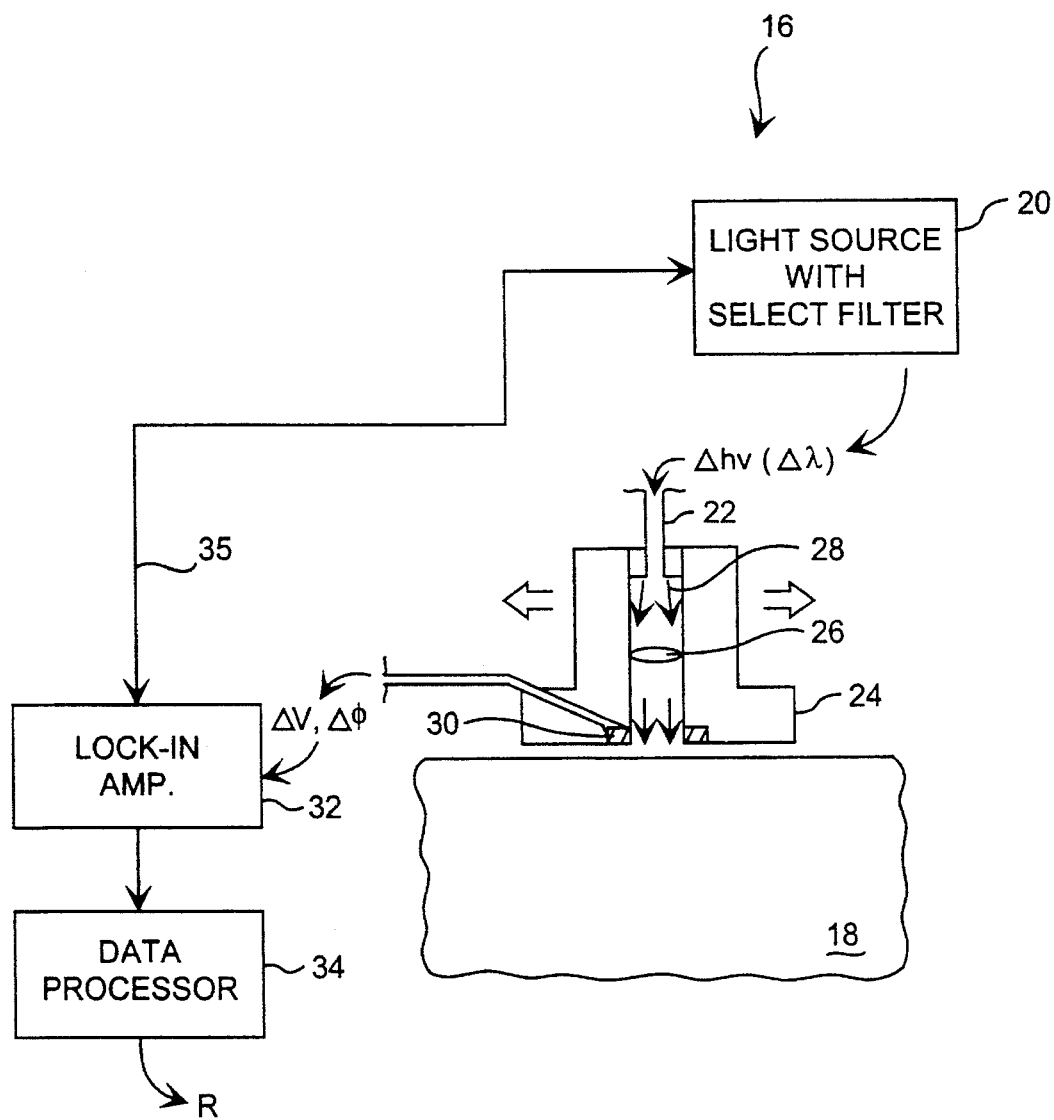
FIG. 2 is a block gram of a device or system for determining a least square correlation factor R of the present invention.

Referring to FIG. 2, a block diagram of a device 16 for detecting changes in photovoltages ΔV and flux values ΔΦ, is illustrated. Specifically, device 16 is used to perform non-destructive, non-contact analysis of defects within a crystallographic substrate 18 using many advantages of SPV techniques. A preferred embodiment of device 16 includes a light source 20 having, for example, a quartz halogen bulb focused through a filter or chopper network for selecting various light intensity values, Δhv. (various wavelengths Δλ) necessary for mapping observed points described herein below.

The filtered and attenuated light beams are sent within a fiber optic cable 22. Cable 22 is fixed within a housing 24 such that the light beams are directed to a lens 26 which focuses the beams 28 as monochromatic light upon the upper surface of substrate 18. Housing 24 can be moved across the substrate in close proximity to the substrate upper surface to determine defects laterally spaced from one another and throughout the substrate. Depending upon the presence or absence of defects within substrate 18, incident light beams 28 will generate a reduced or non-reduced photovoltage, respectively, upon a photo detector 30. At each photon energy hv a resulting photovoltage V will be detected upon the input of lock-in amplifier 32. Lock-in amplifier 32 is placed in phase and synchronized with light source and filter 20 via link 35. Thus, lock-in amplifier 32 assures each photon energy will produce a corresponding photovoltage which either increases monotonically (linearly) or non-monotonically (non-linearly) with increase in photon energy. Lock-in amplifier 32 provides an output of photovoltages at corresponding photon energies to data processor 34. Data processor 34 obtains the inverse or reciprocal of photovoltages as well as absorption coefficients for each photon energy, and maps a set of observed points to a memory array within processor 34. Processor 34 also determines a set of expected points based upon a linear (monotonically increasing) set of points derived from a subset of the observed points. The monotonically increasing points (expected points) are mapped to a separate memory array as a sloped line of expected points plotted along that line. Data processor 34 can then compare the observed points to points along the sloped line to achieve a least square correlation factor R. Magnitude of defects within substrate 18 is inversely proportional to the magnitude of least square correlation factor R. Once R is determined by processor 34, the operator can then quickly ascertain the crystallographic quality of substrate 18. If R is quantified to be less than a pre-determined amount, then the operator can fix substrate 18 as having defects within the crystal lattice. A preferred threshold amount, or pre-determined amount, of least square correlation factor R is approximately 0.98. Thus, whenever R is read to be less than 0.98, then defects within substrate 18 are determined to be present.

Figure 3:
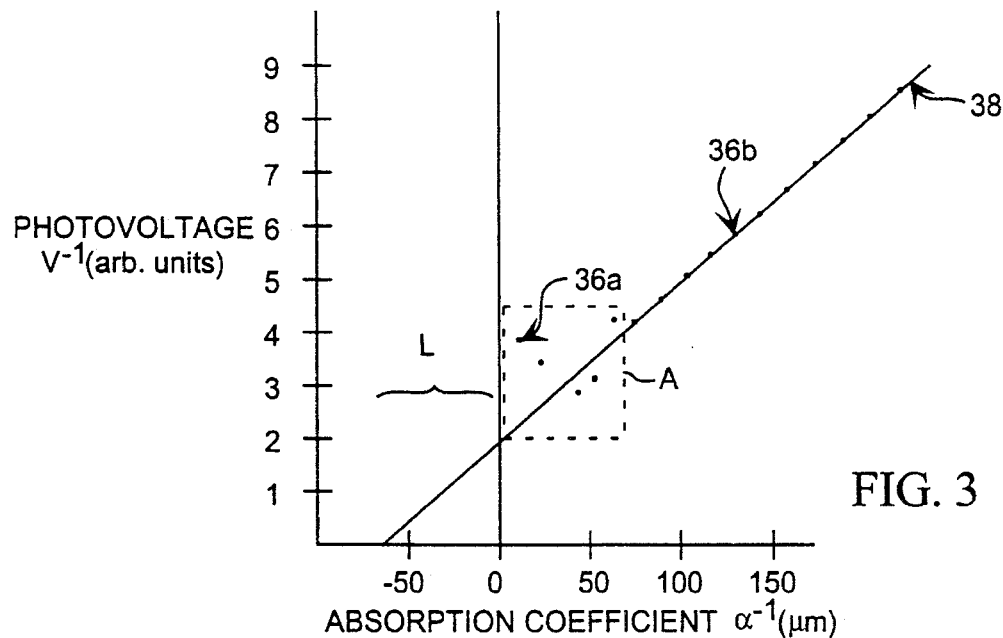
FIG. 3 is a plot of reciprocal photovoltage versus reciprocal absorption coefficient according to the present invention.

Referring now to FIG. 3, a plot of reciprocal photovoltage versus reciprocal absorption coefficient obtained by device 16 is shown. Observed points 36 are mapped upon a plot of reciprocal photovoltage as a function of reciprocal absorption coefficient. Observed points 36a are shown non-monotonic with each other if areas of defects exist within substrate 18. Thus, area A illustrates non-monotonic points 36a which are not aligned with a sloped line 38. Sloped line 38 is a straight line between monotonic, observed points 36b. Line 38, formed between monotonic observed points 36b and extrapolated to a y-axis intercept, provides diffusion length L according to prior designs. However, the present methodology is interested only in areas of positive absorption coefficient and therefore is disinterested in diffusion length L or determination thereof.

Figure 4:
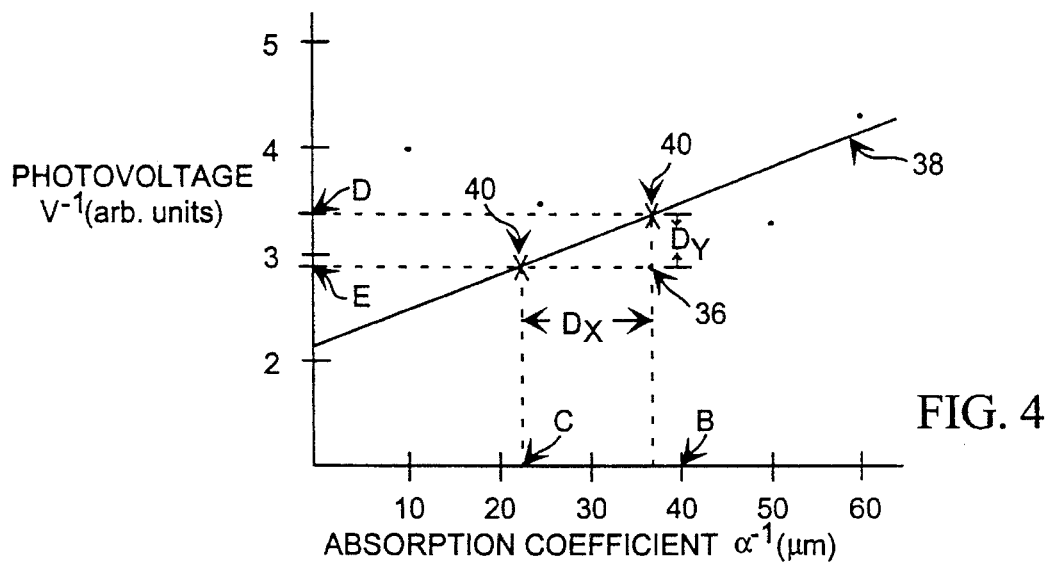
FIG. 4 is a detail view along area A of FIG. 3 showing observed points, expected points and least square correlation therebetween according to the present invention.

Monotonic and non-monotonic observed points 36 are compared with sloped line 38 to determine a least square correlation factor R. FIG. 4 illustrates a comparison methodology within detail area A of FIG. 3. Specifically, observed points 36 are compared with expected points 40 to obtain a difference D therebetween. Expected points 40 represent points which fall along line 38 in a monotonically increasing or decreasing fashion. Thus, if observed points 36 are fairly close to expected points 40, then difference D will be quite small and the resulting least square correlation factor R will be correspondingly close to one.

The method in which data processor 34 determines least square correlation factor R is best illustrated by referencing the example shown in FIG. 4. Difference D is obtained by subtracting expected point 40 from observed point 36 along, for example, reciprocal absorption coefficient axis. Difference $D_x$ using the exemplary reciprocal absorption coefficient values shown in FIG. 4, corresponds to point B (37 μm) minus point C (23 μm) to obtain a difference $D_x=37-23=14$ μm. Difference $D_x$ of value 14 is scaled by a factor of, for example, maximum reciprocal absorption coefficient point B (or 37) by dividing difference $D_x$ of 14 by scaling factor SF (i.e., 37) to obtain a scaled difference less than one (e.g., 14/37). The scaled difference between each expected point and corresponding observed point is then squared to obtain a scaled squared difference (e.g., $(14/37)^2$) for the plurality of differences corresponding to each observed point. Squaring each scaled difference is performed to achieve a scaled squared difference which can be added together with other scaled squared differences (for each of the plurality of differences) to obtain a squared sum which totals less than one. The square root of the squared sum can then be taken to achieve a residual least square correlation factor. The residual least square correlation factor is then subtracted from one to produce a least square correlation factor. Thus, least square correlation factor R is determined by the following equation:

$$R = 1 - \sqrt{\left(\frac{D_1}{SF}\right)^2 + \left(\frac{D_2}{SF}\right)^2 + \ldots}$$

The above least square correlation methodology is best suited for quickly determining, via processor 34, the correlation between observed points 36 and expected points 40. If observed points 36 correspond identically to expected points 40, then R will be equal to a unit one. Slight differences in correlation will reduce the R amount to less than one, whereas larger deviations will reduce R substantially below one. Accordingly, an R factor less than a pre-determined amount corresponds to substrate areas having crystallographic defects. It is understood from the above example used in determining least square correlation factor R, that instead of determining difference $D_x$, difference $D_y$ can be used. As such, point E can be subtracted from point D and point D be used as a scaling factor SF.

Figure 5:
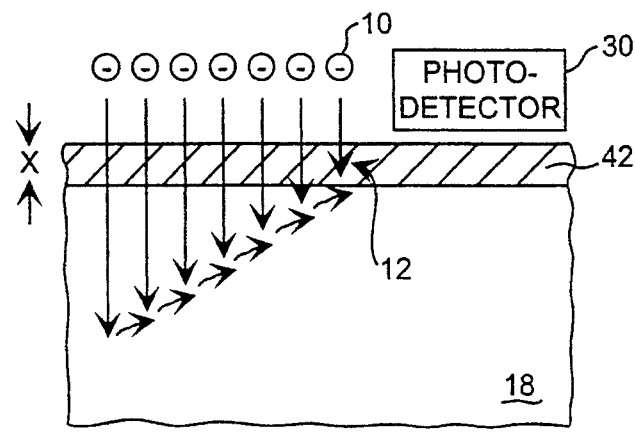
FIG. 5 is a cross-sectional view of a crystallographic substrate with defects therein detectable by injected electrons (photon energies) and resulting photovoltage according to the present invention.

Referring now to FIG. 5, determination of defects within crystalline substrate 18 is illustrated as a cross-sectional view of substrate 18 having a defect region 42 shown at or near the surface of substrate 18. Defect region 42 may, for example, correspond to an amorphous region created by ion implantation. Increase in defect region 42 or density of defects in region 42 will cause a corresponding decrease in photovoltage at the surface of substrate 18, as detected by photodetector 30. Photon energy of injected carriers 10 can be adjusted to extend beyond region 42 and, based upon the amount of energy upon carrier 10, relative depth X can be ascertained. If, for example, photon energies are such that carriers 10 do not inject past region 42, then substantially all of the carriers will lack recombination with minimal production of surface photovoltage. Conversely, if photon energies upon carriers 10 are such that almost all carriers extend below region 42, then photovoltage upon detector 30 will remain quite high. By monitoring the amount of photon energy injected into the substrate, corresponding depth of region 42 can be measured.

Figure 6:
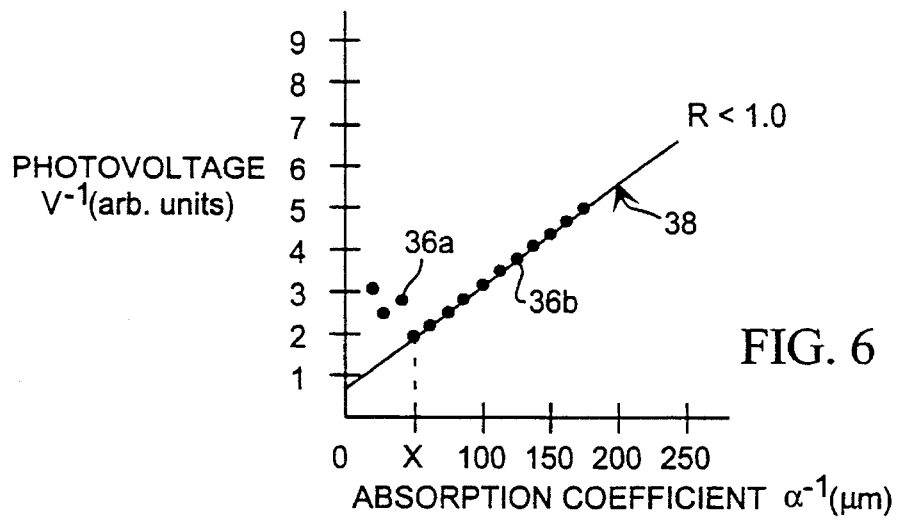
FIGS. 6–8 are plots of reciprical photovoltage versus reciprocal absorption coefficient for various least square correlation factors R throughout a substrate and at various ranges within the substrate, all of which are detectable according to the present invention.

Referring now to FIG. 6, observed points 36 are illustrated in a plot of reciprocal photovoltage versus reciprocal absorption coefficient. Non-monotonic points 36a add to the difference between those points and expected points plotted along line 38, wherein line 38 comprises a line connecting monotonic observed points 36b and extrapolated to a zero reciprocal absorption coefficient value. A demarcation occurs between monotonic points 36b and non-monotonic points 36a, as represented by distance X. Distance X can be extrapolated from (or correlated to) reciprocal absorption coefficient. Distance X, as shown in FIG. 5, represents a thickness region 42 of defective crystalline material within substrate 18. Thus, depending upon the relative thickness and magnitude of defects within region 42, residual least square correlation factor R can be fairly close to but less than a unit one. The amount of difference between unit one and the actual R value can be correlated to the magnitude of defects within substrate 18 (or the thickness of defective region 42 within substrate 18).

Figure 7:
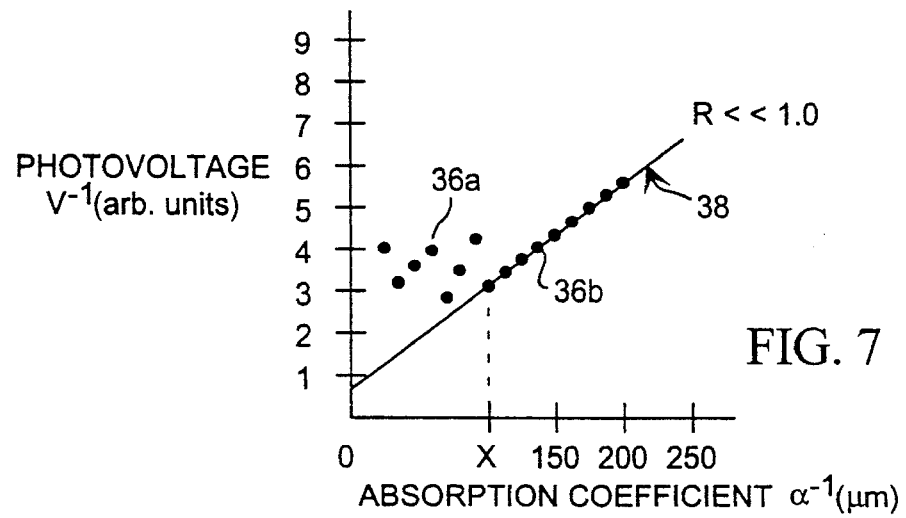

If region 42 increases in thickness, and distance X correspondingly increases, least square correlation factor R decreases substantially below one as shown in FIG. 7. FIG. 7 illustrates numerous observed points 36a of non-monotonic value which add to the difference between observed points 36a and corresponding expected points upon line 38. Increase in the difference between such points increases the corresponding residual least square correlation factor for the squared sum of differences thereby producing a lower least square correlation factor R for the entire range of values shown.

Figure 8:
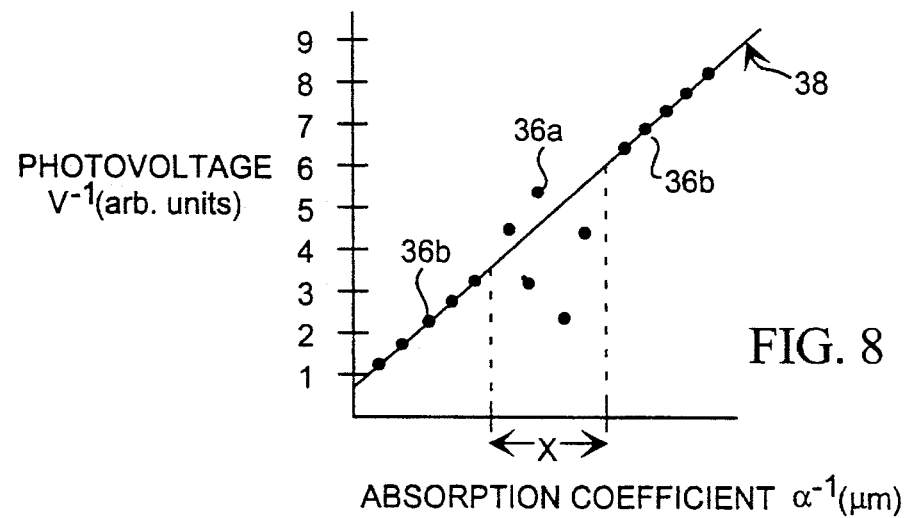

Referring to FIG. 8, it is appreciated from said figure that photon energies of minority carriers impinging upon substrate 18 can vary to a high resolution value and to high enough energies to penetrate at a substantial depth within substrate 18. High energy, high resolution values can be used to obtain demarcation between monotonic and non-monotonic points 36b and 36a, respectively. Demarcation, or change in linearity, between such points for various photon energy and corresponding carrier injection depths, allows the operator to ascertain the presence of defects within an embedded region X within substrate 18. Thus, an embedded region of defects 42 can be detected provided photon energies are sufficient to reach the embedded regions. Not only will least square correlation factor R be quite low (substantially less than one) but processor 34 can be used to map points 36a with respect to a select depth within substrate 18. FIG. 8 illustrates one example in which layer 42 of defects X are shown. However, it is understood that numerous layers or ranges of possibly several regions 42 containing crystallographic defects can be ascertained in accordance with the spirit and scope of the present invention.

It will be appreciated to those skilled in the art having the benefit of this disclosure that this invention is capable of applications with numerous types of crystallographic substrate material including, for example, a substrate of crystalline silicon used in the manufacture of integrated circuits. Furthermore, it is to be understood that the form of the invention shown and described is to be taken as a presently preferred embodiment. Various modifications and changes may be made to the SPV technique and methodology as would be obvious to a person skilled in the art after having the benefit of this disclosure. It is intended that the following claims be interpreted to embrace all such modifications and changes and, accordingly, the specification and drawings are to be regarded in an illustrative rather than a restrictive sense.

What is claimed is:

1. A method for determining defects within a crystallographic substrate comprising the steps of:

radiating a crystallographic semiconductor substrate with a plurality of dissimilar photon energies to produce a respective plurality of reciprocal photovoltages;

determining a plurality of reciprocal absorption coefficients corresponding to respective said plurality of photovoltages;

mapping a set of observed points, wherein each of said set of observed points corresponds to one of said plurality of photovoltages plotted as a function of a respective one of said plurality of absorption coefficients;

computing a least square correlation factor between said set of observed points and a sloped line; and ascertaining the presence of defects within said semiconductor substrate based upon the magnitude of said least square correlation factor being less than a pre-determined amount.

2. The method as recited in claim 1, wherein said mapping step comprises plotting said plurality of photovoltages as a function of respective said plurality of absorption coefficients, wherein each photovoltage and respective absorption coefficient corresponds to one of said plurality of dissimilar photon energies.

3. The method as recited in claim 1, wherein said computing step comprises:

obtaining a set of expected points along said sloped line for each of said plurality of photovoltages; and calculating a plurality of differences between each said expected point and corresponding said observed point, dividing each said difference by a scaling factor to obtain a scaled difference less than one, squaring each said scaled difference to obtain a scaled squared difference, and adding said scaled squared difference for each of said plurality of differences to obtain a squared sum totaling less than one;

taking the square root of said squared sum to obtain a residual least square correlation factor; and subtracting said residual least square correlation factor from one to produce said least square correlation factor.

4. The method as recited in claim 1, wherein said predetermined amount is approximately equal to 0.98.

5. The method as recited in claim 1, wherein said mapping step comprises excluding all said observed points having respective said reciprocal absorption coefficients less than 0 µm.

6. The method as recited in claim 1, wherein said mapping step comprises including all said observed points having respective said reciprocal absorption coefficients greater than 0 µm, regardless of whether said observed points are monotonically increasing.

7. The method as recited in claim 1, further comprising:

computing a select least square correlation factor at a specified range along said sloped line;

correlating said specified range to a respective layer of thickness X within said semiconductor substrate; and ascertaining the presence of defects within said layer of thickness X based upon the magnitude of said select least square correlation factor being less than a pre-determined amount.

8. A method for determining defects within a crystallographic substrate comprising the steps of:

radiating a crystallographic semiconductor substrate with beams of monochromatic radiation having different photon energies to produce a respective plurality of reciprocal photovoltages;

detecting said plurality of photovoltages as a function of respective plurality of reciprocal absorption coefficients; mapping a set of observed points corresponding to said plurality of photovoltages as a function of respective said plurality of absorption coefficients;

computing a least square correlation factor between said set of observed points and a sloped line, comprising:

obtaining a set of expected points along said sloped line for each of said plurality of photovoltages;

calculating a plurality of differences between each said expected point and corresponding said observed point, dividing each said difference by a scaling factor to obtain a scaled difference less than one, squaring each said scaled difference to obtain a scaled squared difference, and adding said scaled squared difference for each of said plurality of differences to obtain a squared sum totaling less than one;

taking the square root of said squared sum to obtain a residual least square correlation factor;

subtracting said residual least square correlation factor from one to produce said least square correlation factor; and ascertaining the presence of defects within said semiconductor substrate based upon the magnitude of said least square correlation factor being less than a pre-determined amount.

9. The method as recited in claim 8, wherein said predetermined amount is approximately equal to 0.98.

10. The method as recited in claim 8, wherein said mapping step comprises excluding all said observed points having respective said reciprocal absorption coefficients less than 0 µm.

11. The method as recited in claim 8, wherein said mapping step comprises including all said observed points having respective said reciprocal absorption coefficients greater than 0 µm, regardless of whether said observed points are monotonically increasing.

12. The method as recited in claim 8, further comprising:

computing a select least square correlation factor at a specified range along said sloped line;

correlating said specified range to a respective layer of thickness X within said semiconductor substrate; and ascertaining the presence of defects within said layer of thickness X based upon the magnitude of said select least square correlation factor being less than a predetermined amount.

13. A device for determining defects within a semiconductor substrate comprising:

a light source adapted to produce a plurality of light beams at dissimilar wavelengths;

a housing connected to said light source and capable of movement across an upper surface of a semiconductor substrate, said housing is adapted to receive a fiber optic cable containing said plurality of light beams and further adapted to house a photodetector for producing a respective plurality of reciprocal photovoltages responsive to said light beams directed upon said upper surface;

a lock-in amplifier connected to said housing and said light source for locking in said photovoltages with phase of respective light beam wavelengths;

a data processor connected to said lock-in amplifier for (i) compiling a set of expected points upon a straight line, (ii) mapping a set of observed points corresponding to said plurality of photovoltages, (iii) computing a least square correlation factor between said set of observed points and respective said set of expected points, and (iv) ascertaining the presence of defects within said semiconductor substrate based upon the magnitude of said least square correlation factor being less than a pre-determined amount.

14. The device as recited in claim 13, wherein said least square correlation factor is approximately equal to 0.98.

15. The device as recited in claim 13, wherein said data processor comprises a computer adapted to exclude all observed points which have a reciprocal absorption coefficient less than 0 µm.

16. The device as recited in claim 13, wherein said mapping step comprises including all said observed points having a respective reciprocal absorption coefficient greater than 0 µm, regardless of whether said observed points are monotonically increasing.

* * * * *